US007967751B2

(12) United States Patent
Goscha et al.

(10) Patent No.: US 7,967,751 B2
(45) Date of Patent: *Jun. 28, 2011

(54) AMBULATORY REPEATER FOR USE IN AUTOMATED PATIENT CARE

(75) Inventors: Donald L. Goscha, Elk River, MN (US); Lisa D. Haeder, New Hope, MN (US); Veerichetty A. Kadhiresan, Centerville, MN (US); David C. Johnson, Inver Grove Heights, MN (US); Muralidharan Srivathsa, Shoreview, MN (US); Marina Brockway, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 307 days.

This patent is subject to a terminal disclaimer.

(21) Appl. No.: 11/893,704

(22) Filed: Aug. 17, 2007

(65) Prior Publication Data

US 2007/0288069 A1 Dec. 13, 2007

Related U.S. Application Data

(62) Division of application No. 11/113,206, filed on Apr. 22, 2005, now Pat. No. 7,270,633.

(51) Int. Cl.
*A61B 5/00* (2006.01)
(52) U.S. Cl. ...................... 600/300; 607/60; 340/539.12
(58) Field of Classification Search .................. 600/300, 600/301; 128/903–905, 920
See application file for complete search history.

(56) References Cited

U.S. PATENT DOCUMENTS

| | | | |
|---|---|---|---|
| 5,307,263 A | 4/1994 | Brown | |
| 5,721,777 A | 2/1998 | Blaze | |
| 6,024,699 A | 2/2000 | Surwit et al. | |
| 6,083,248 A | 7/2000 | Thompson | |
| 6,171,256 B1 | 1/2001 | Joo et al. | |

(Continued)

OTHER PUBLICATIONS

Health Insurance Portability And Accountability Act of 1996, Pub. L. No. 104-191, 110 Stat. 1936 (Aug. 21, 1996).
E. Hammond, "National Committee On Vital And Health Statistics, Subcommittee On Health Data Needs, Standards And Security." http://www.ncvhs.hhs.gov/970211t3.htm, pp. 1-4 (Feb. 11, 1997).
Security And Electronics Signature Standards; Proposed Rule, Federal Register, vol. 63, No. 155 (Aug. 12, 1998).

(Continued)

*Primary Examiner* — Henry M Johnson, III
*Assistant Examiner* — Kai Rajan
(74) *Attorney, Agent, or Firm* — Pauly, DeVries Smith & Deffner, L.L.C.

(57) ABSTRACT

An ambulatory repeater for use in automated patient care is presented. A local memory store includes a cryptographic key, sensitive information, and physiological measures. The cryptographic key is uniquely assigned to the implantable medical device prior to implant of the implantable medical device into a patient. The sensitive information is preencrypted under the cryptographic key and physiological measures are measured by the implantable medical device. An authentication module is in receipt of the cryptographic key. A permissions module confirms authorization of an external data processing device against the cryptographic key. A decryption module decrypts the sensitive information with the cryptographic key into decrypted information. A processor is operatively coupled to the local memory store. A communications module exchanges the decrypted information and the physiological measures with the external data processing device over a wireless interface contingent upon the authorization confirmation. An internal power supply supplies power to the foregoing components.

16 Claims, 11 Drawing Sheets

U.S. PATENT DOCUMENTS

| | | | |
|---|---|---|---|
| 6,336,903 B1 | 1/2002 | Bardy | |
| 6,368,284 B1 | 4/2002 | Bardy | |
| 6,398,728 B1 | 6/2002 | Bardy | |
| 6,411,840 B1 | 6/2002 | Bardy | |
| 6,416,471 B1 | 7/2002 | Kumar et al. | |
| 6,440,066 B1 | 8/2002 | Bardy | |
| 6,456,256 B1 | 9/2002 | Amundson et al. | |
| 6,493,587 B1* | 12/2002 | Eckmiller et al. | 607/31 |
| 6,497,655 B1 | 12/2002 | Linberg et al. | |
| 6,513,532 B2 | 2/2003 | Mault et al. | |
| 6,574,510 B2 | 6/2003 | Von Arx et al. | |
| 6,614,406 B2 | 9/2003 | Amundson et al. | |
| 6,827,670 B1 | 12/2004 | Stark et al. | |
| 6,893,396 B2* | 5/2005 | Schulze et al. | 600/300 |
| 7,009,511 B2 | 3/2006 | Mazar et al. | |
| 7,027,872 B2 | 4/2006 | Thompson | |
| 7,039,810 B1* | 5/2006 | Nichols | 713/182 |
| 7,155,290 B2 | 12/2006 | Von Arx et al. | |
| 7,475,245 B1 | 1/2009 | Healy et al. | |
| 7,801,611 B2* | 9/2010 | Persen et al. | 607/31 |
| 2001/0027331 A1* | 10/2001 | Thompson | 607/60 |
| 2004/0260363 A1* | 12/2004 | Arx et al. | 607/60 |
| 2005/0204134 A1 | 9/2005 | Von Arx et al. | |
| 2008/0117954 A1 | 5/2008 | Chuang et al. | |

OTHER PUBLICATIONS

"Biotronik Announces First U.S. Implantation of the New BEIos VR-T ICD with Home Monitoring Technology", *Publication: Business Wire* May 3, 2002, pp. 1-5.

"Home Monitoring System", *Premarket Approval (PMA) Database, U.S. Food and Drug Administration, Center for Devices and Radiological Health* Jul. 8, 2008, pp. 1-2.

"Home Monitoring System with BA03 DDDR Pulse Generator—P950037/S19", *U.S. Food and Drug Administration, Center for Devices and Radiological Health* Oct. 31, 2001, pp. 1-2.

"Home Monitoring System, including BA03 DDDR Pulse Generator, RUC 200 Patient Device, and B-KT0.0.A Programmer Software", *Department of Health and Human Services*, letter dated Oct. 11, 2001, pp. 1-7.

"FDA Approves New Type of Pacemaker", *U.S. Food and Drug Administration, FDA Talk Paper, T01-47* Oct. 11, 2001, pp. 1-2.

File History for co-pending U.S. Appl. No. 11/901,520, filed Sep. 17, 2007 (360 pages).

Partial File History (from Sep. 24, 2010 to present) for co-pending U.S. Appl. No. 11/901,520, filed Sep. 17, 2007, entitled "An External Data Processing Device to Interface with an Ambulatory Repeater and Method Thereof" (38 pages).

* cited by examiner

190

200

AMBULATORY REPEATER FOR USE IN AUTOMATED PATIENT CARE

CROSS-REFERENCE TO RELATED APPLICATION

This patent application is a divisional of U.S. patent application Ser. No. 11/113,206, filed Apr. 22, 2005, now U.S. Pat. No. 7,270,633, issued Sep. 18, 2007, the priority of filing date of which is claimed, and the disclosure of which is incorporated by reference.

FIELD

The present invention relates in general to automated patient care and, specifically, to an ambulatory repeater for use in automated patient care.

BACKGROUND

In general, implantable medical devices (IMDs) provide in situ therapy delivery, such as pacing, cardiac resynchronization, defibrillation, neural stimulation and drug delivery, and physiological monitoring and data collection. Once implanted, IMDs function autonomously by relying on pre-programmed operation and control over therapeutic and monitoring functions. IMDs can be interfaced to external devices, such as programmers, repeaters and similar devices, which can program, troubleshoot, and download telemetered data, typically through induction or similar forms of near-field telemetry.

Telemetered data download typically occurs during follow-up, which requires an in-clinic visit by the patient once every three to twelve months, or as necessary. Following interrogation of the IMD, the telemetered data can be analyzed to evaluate patient health status. Although clinical follow-up is mandatory, the frequency and type of follow-up are dependent upon several factors, including projected battery life, type, mode and programming of IMD, stability of pacing and sensing, the need for programming changes, underlying rhythm or cardiac condition, travel logistics, and the availability of alternative follow-up methods, such as transtelephonic monitoring, for example, the CareLink Monitor, offered by Medtronic, Inc., Minneapolis, Minn.; Housecall Plus Remote Patient Monitoring System, offered by St. Jude Medical, Inc., St. Paul, Minn.; and BIOTRONIK Home Monitoring Service, offered by BIOTRONIK GmbH & Co. KG, Berlin, Germany.

Telemetered data generally includes information on all programmed device parameters, as well as real time or measured and recorded data on the operation of the IMD available at the time of interrogation. In addition, telemetered data can include parametric and physiological information on the output circuit, battery parameters, sensor activities for rate adaptive IMDs, event markers, cumulative totals of sensed and paced events, and transmission of electrograms. Derived measures include battery depletion, which can be gauged by the downloaded battery voltage and impedance levels, and lead integrity, which is reflected by pacing impedance. Event markers depict pacing and sensing simultaneously recorded with electrograms to indicate how the IMD interprets specifically paced or sensed events with timing intervals. Other types of telemetered data are possible.

Clinical follow-up is conventionally performed using a programmer under the direction of trained healthcare professionals. The programmer is typically interfaced to an IMD through inductive near field telemetry. Fundamentally, IMDs are passive devices that report on operational and behavioral patient status, including the occurrence of significant events, only when interrogated by an external device. As a result, the programmer-based follow-up sessions generally provide the sole opportunity for the IMD to report any significant event occurrences observed since the last follow-up session. Moreover, the latency in reporting significant event occurrences becomes dependent upon the timing of the clinical follow-up sessions for non-closely followed patients. Thus, in some circumstances, delays in downloading telemetered data can result in lost data or chronic cardiac conditions recognized too late.

Recently, far field telemetry using radio frequency (RF) carrier signals has provided an alternative means for interfacing programmers and similar external devices to IMDs, such as described in commonly-assigned U.S. Pat. No. 6,456,256, issued Sep. 24, 2002, to Amudson et al.; U.S. Pat. No. 6,574,510, to Von Arx et al., issued Jun. 3, 2003; and U.S. Pat. No. 6,614,406, issued Sep. 2, 2003, to Amudson et al., disclosures of which are incorporated by reference. Far field telemetry has a higher data rate, which results in shorter downloading times, and the patient experiences greater freedom of movement while the IMD is being accessed. Nevertheless, despite the higher data rate, the IMD remains a passive device that only reports significant event occurrences when interrogated using an RF-capable programmer.

Similarly, dedicated monitoring devices, known as repeaters, have become available to patients to provide monitoring and IMD follow-up in an at-home setting similar to transtelephonic monitoring. Each repeater is specifically matched to an IMD. Once a day or as required, the patient uses the repeater to actively poll the IMD through induction or far field telemetry. Alternatively, some repeaters can be passively polled. During each session, any significant events occurrences are reported, although programming of the IMD is generally not allowed for safety reasons. As well, repeaters download recorded telemetered data. Despite the improved frequency and speed of telemetered data downloads, the latency to report significant event occurrences can be as long as a full day. The patient must also be physically proximal to the repeater during interrogation in the same fashion as a programmer. In addition, repeaters, by virtue of being stationary devices, are unable to capture patient physiological and behavioral data while the patient is engaged in normal everyday activities or at any other time upon the initiation of the patient or by a remote patient management system.

Furthermore, the use of RF telemetry in IMDs potentially raises serious privacy and safety concerns. Sensitive information, such as patient-identifiable health information (PHI), exchanged between an IMD and the programmer or repeater should be safeguarded to protect against compromise. Recently enacted medical information privacy laws, including the Health Insurance Portability and Accountability Act (HIPAA) and the European Privacy Directive underscore the importance of safeguarding a patient's privacy and safety and require the protection of all patient-identifiable health information (PHI). Under HIPAA, PHI is defined as individually identifiable health information, including identifiable demographic and other information relating to the past, present or future physical or mental health or condition of an individual, or the provision or payment of health care to an individual that is created or received by a health care provider, health plan, employer or health care clearinghouse. Other types of sensitive information in addition to or in lieu of PHI could also be protectable.

The sweeping scope of medical information privacy laws, such as HIPAA, may affect patient privacy on IMDs with longer transmission ranges, such as provided through RF telemetry, and other unsecured data interfaces providing sensitive information exchange under conditions that could allow eavesdropping, interception or interference. Sensitive information should be encrypted prior to long range transmission. Currently available data authentication techniques for IMDs can satisfactorily safeguard sensitive information. These techniques generally require cryptographic keys, which are needed by both a sender and recipient to respectively encrypt and decrypt sensitive information transmitted during a data exchange session. Cryptographic keys can be used to authenticate commands, check data integrity and, optionally, encrypt sensitive information, including any PHI, during a data exchange session. Preferably, the cryptographic key is unique to each IMD. However, authentication can only provide adequate patient data security if the identification of the cryptographic key from the IMD to the programmer or repeater is also properly safeguarded.

Therefore, there is a need for an approach to providing an ambulatory solution to retrieving physiological and parametric telemetered data from IMDs. Preferably, such an approach would provide authenticated and secure communication with IMDs and include configurable activation settings.

SUMMARY

A system and method provide an ambulatory repeater for securely exchanging information, including sensitive patient data, between an implantable medical device and one or more external data processing devices, such as a base repeater, server, or programmer. The ambulatory repeater is interfaced to one or more external sensors to provide the capability to directly monitor patient health information at any time. The ambulatory repeater includes a power supply for operating separately and independently from an external power source and can be held or worn by a patient. The ambulatory repeater interrogates the IMD over a secure data connection on a regular basis or on demand and interfaces periodically to the external data processing device to exchange the information retrieved from the implantable medical device.

One embodiment provides a secure wireless ambulatory repeater. A cryptographic key is uniquely assigned to an implantable medical device. Sensitive information is preencrypted under the cryptographic key. Physiological measures are measured by the implantable medical device. A decryption module decrypts the sensitive information with the cryptographic key into decrypted information. A communications module exchanges the decrypted information and the physiological measures with the external data processing device over a wireless interface contingent upon authorization of the external data processing device.

A further embodiment provides an ambulatory repeater for use in automated patient care. A local memory store includes a cryptographic key, sensitive information, and physiological measures. The cryptographic key is uniquely assigned to the implantable medical device prior to implant of the implantable medical device into a patient. The sensitive information is preencrypted under the cryptographic key and physiological measures are measured by the implantable medical device. An authentication module is in receipt of the cryptographic key. A permissions module confirms authorization of an external data processing device against the cryptographic key. A decryption module decrypts the sensitive information with the cryptographic key into decrypted information. A processor is operatively coupled to the local memory store. A communications module exchanges the decrypted information and the physiological measures with the external data processing device over a wireless interface contingent upon the authorization confirmation. An internal power supply supplies power to the foregoing components.

A further embodiment provides a system for applying an ambulatory repeater to secure information exchange in automated patient care. An implantable medical device is implanted into a patient. A cryptographic key is uniquely assigned prior to implant. Sensitive information is preencrypted under a cryptographic key. Physiological measures are measured on an ad hoc basis by a sensor. An ambulatory repeater includes a storage, which stores the cryptographic key. A permissions module confirms authorization of an external data processing device against the cryptographic key. A decryption module decrypts the sensitive information with the cryptographic key into decrypted information. An external data processing device includes an interrogator receiving the decrypted information and the physiological measures from the ambulatory repeater over a wireless interface contingent upon the authorization confirmation.

Still other embodiments of the present invention will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Implantable Medical Device

Figure 1:
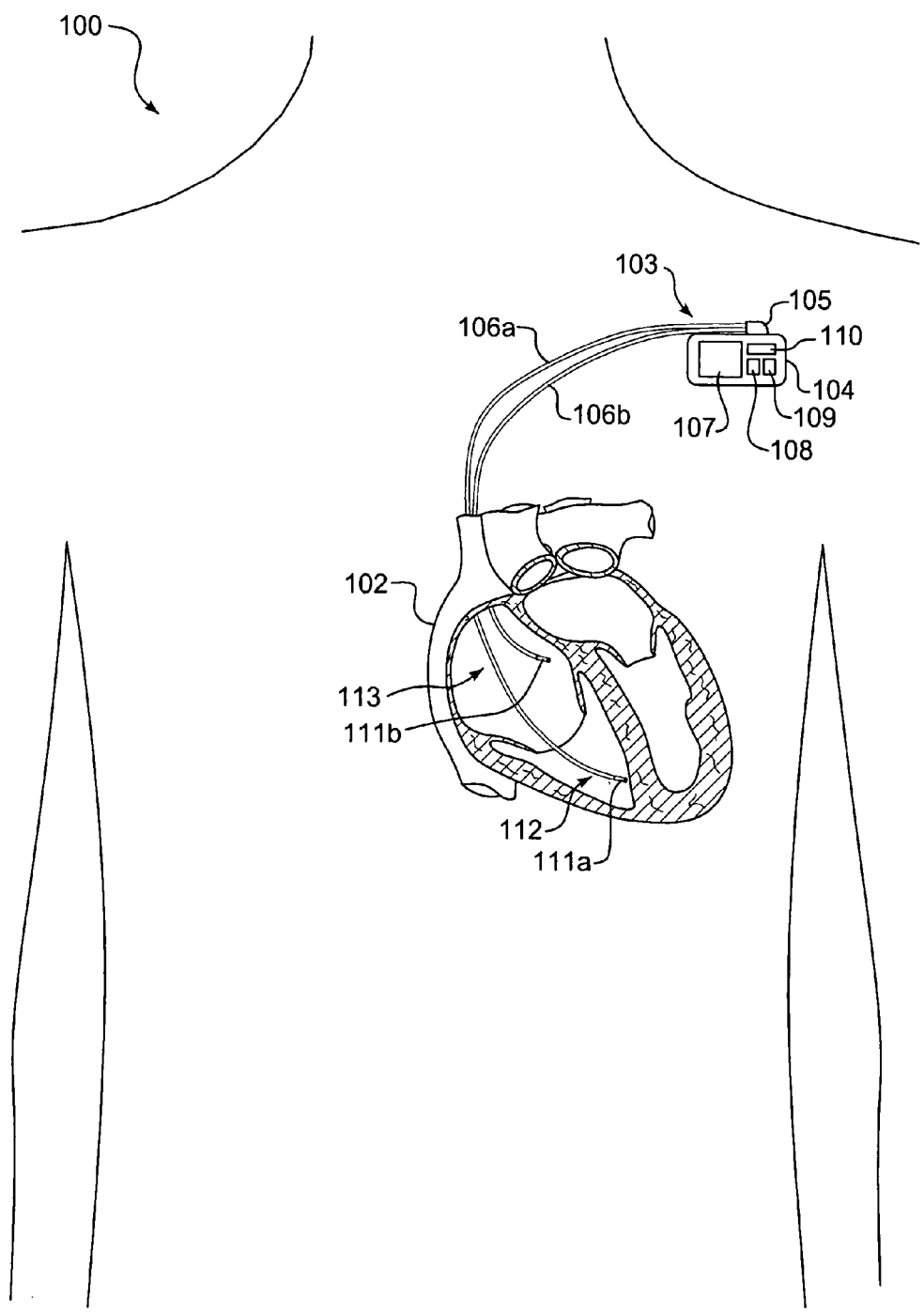
FIG. 1 is a block diagram showing, by way of example, an implantable medical device.

FIG. 1 is a block diagram showing, by way of example, an implantable medical device (IMD) 103. The IMD 103, such as a pacemaker, implantable cardiac defibrillator (ICD) or similar device, is surgically implanted in the chest or abdomen of a patient to provide in situ therapy, such as pacing, cardiac resynchronization, defibrillation, neural stimulation and drug delivery, and physiological data monitoring. Examples of cardiac pacemakers suitable for use in the described embodiment include the Pulsar Max II, Discovery, and Discovery II pacing systems and the Contak Renewal cardiac resynchronization therapy defibrillator, sold by Guidant Corporation, St. Paul, Minn.

The IMD 103 includes a case 104 and terminal block 105 coupled to a set of leads 106a-b. The leads 106a-b are implanted transvenously for endocardial placement. The IMD 103 is in direct electrical communication with the heart 102 through electrodes 111a-b positioned on the distal tips of each lead 106a-b. By way of example, the set of leads 106a-b can include a right ventricular electrode 111a, preferably placed in the right ventricular apex 112 of the heart 102, and a right atrial electrode 111b, preferably placed in the right atrial chamber 113 of the heart 102. The set of leads 106a-b can also include a right ventricular electrode 114a and a right atrial electrode 114b to enable the IMD 103 to directly collect physiological measures, preferably through millivolt measurements.

The IMD 103 includes a case 104 and terminal block 105 coupled to a set of leads 106a-b. The IMD case 104 houses hermitically-sealed components, including a battery 107, control circuitry 108, memory 109, and telemetry circuitry 110. The battery 107 provides a finite, power source. The control circuitry 108 controls therapy delivery and monitoring, including the delivery of electrical impulses to the heart 102 and sensing of spontaneous electrical activity. The memory 109 includes a memory store in which the physiological signals sensed by the control circuitry 108 can be temporarily stored, pending telemetered data download.

The telemetry circuitry 110 provides an interface between the IMD 103 and an external device, such as a programmer conventional or ambulatory repeater, or similar device. For near field data exchange, the IMD 103 communicates with a programmer or conventional or ambulatory repeater (not shown) through inductive telemetry signals exchanged through a wand placed over the location of the IMD 103. Programming or interrogating instructions are sent to the IMD 103 and the stored physiological signals are downloaded into the programmer or repeater. For far field data exchange, the IMD 103 communicates with an external device capable of far field telemetry, such as a radio frequency (RF) programmer, conventional or ambulatory repeater, or other wireless computing device, as further described below with reference to FIG. 2. Other types of data interfaces are possible, as would be appreciated by one skilled in the art.

Other configurations and arrangements of leads and electrodes can also be used. Furthermore, although described with reference to IMDs for providing cardiac monitoring and therapy delivery, suitable IMDs also include other types of implantable therapeutic and monitoring devices in addition to or in lieu of cardiac monitoring and therapy delivery IMDs, including IMDs for providing neural stimulation, drug delivery, and physiological monitoring and collection.

Process Flow

Figure 2:
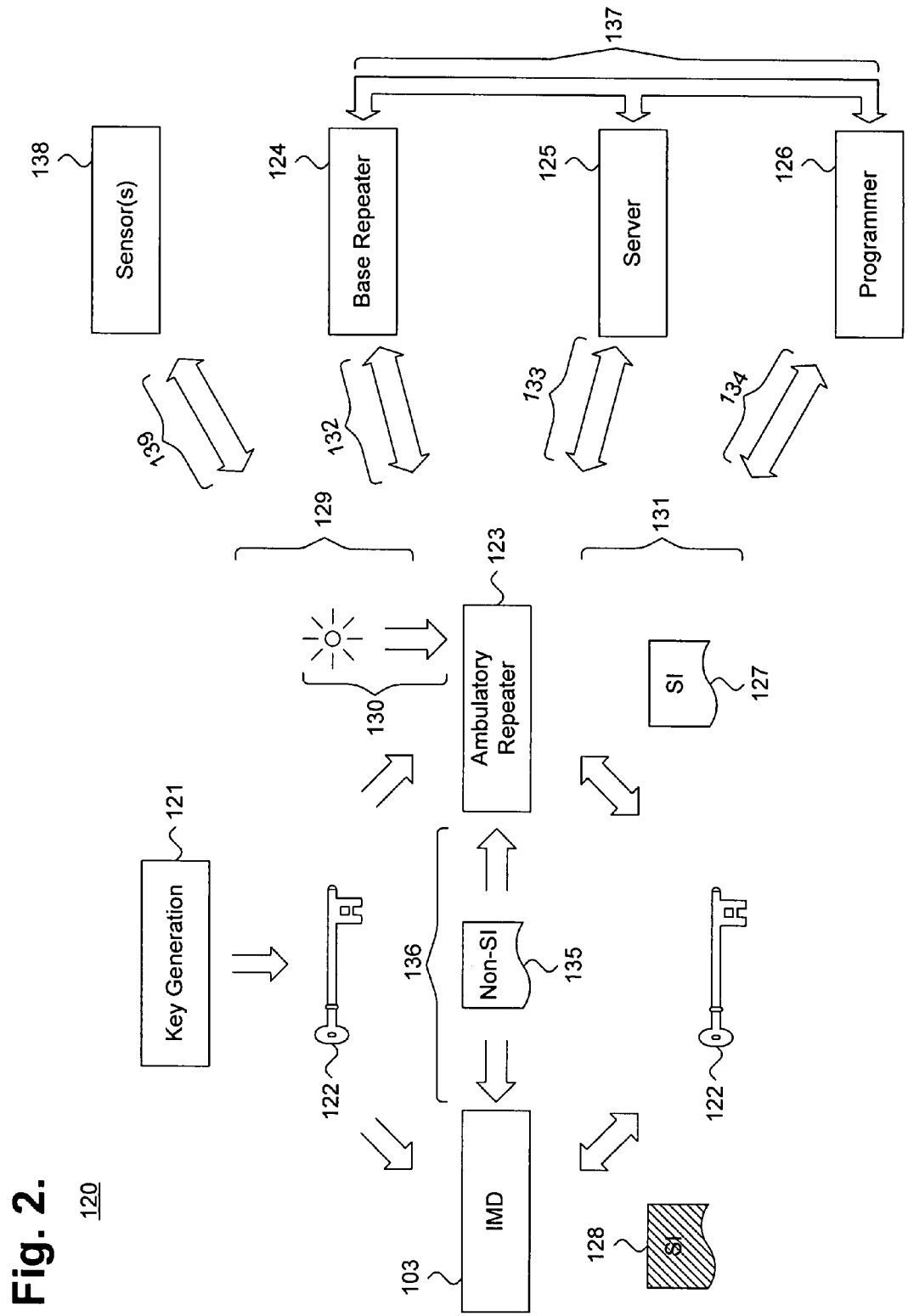
FIG. 2 is a process flow diagram showing interfacing with the implantable medical device of FIG. 2 using an ambulatory repeater.

FIG. 2 is a process flow diagram 120 showing interfacing with the IMD 103 of FIG. 2 using an ambulatory repeater 123. The ambulatory repeater 123 provides a portable means for securely transacting a data exchange session with the IMD 103 and, in turn, at least one of a conventional or "base" repeater 124, server 125, or programmer 126, as further described below with reference to FIG. 5. Unlike a base repeater 124, the ambulatory repeater 123 can collect patient health information as frequently or infrequently as needed and, due to being immediately proximate to the patient, can measure the activity level of the patient during normal everyday activities, rather than only at home or in a clinical setting.

Interfacing 120 with the IMD 103 includes key generation 121, authentication 129, activation 130, protected data storage and retrieval 131, unprotected data storage and retrieval 136, and optional data exchanges 132, 133, 134 with the base repeater 124, server 125, and programmer 126. Key generation 121 creates a cryptographic key 122, which is used to encrypt and decrypt any sensitive information exchanged with the IMD 103, such as during protected data storage and retrieval 131 using long range telemetry or over any other unsecured interface. The cryptographic key 122 can be statically generated and persistently stored, dynamically generated and persistently stored, dynamically generated and non-persistently stored as a session cryptographic key 122, or a combination of the foregoing. Persistently-stored cryptographic keys 122 are maintained in a fixed secure key repository, such as a programmer, patient designator, secure database, token, base repeater 124, ambulatory repeater 123, and on the IMD 103 itself. Statically generated and persistently-stored cryptographic keys are stored in the IMD 103 prior to implantation, such as during the manufacturing process. Dynamically generated and persistently-stored cryptographic keys are generated dynamically, such as by the ambulatory repeater 123 for subsequent download to the IMD 103 using short range telemetry following implantation. Dynamically generated and non-persistently-stored session cryptographic keys are also generated dynamically and shared with the IMD 103, but are not persistently stored and are used for a single patient data exchange. Each cryptographic key 122 is uniquely assigned to the IMD 103. In one embodiment, the cryptographic key 103 has a length of 128 bits, is symmetric or is both 128-bits long and symmetric. Other cryptographic key lengths and symmetries are possible.

Authentication 129 provides an opportunity to securely obtain the cryptographic key 122 uniquely assigned to the IMD 103. In one embodiment, the IMD 103 interfaces with an external source, such as the ambulatory repeater 123 or other wireless computing device, to either receive or share the cryptographic key 122 assigned to the IMD 103, such as described in commonly-assigned U.S. Pat. No. 7,838,828, issued Nov. 9, 2010, the disclosure of which is incorporated by reference. In a further embodiment, the ambulatory repeater 123 retrieves the cryptographic key 122 from the IMD 103 using secure, short range telemetry, such as inductive telemetry, as further described below with reference to FIG. 5.

In a further embodiment, the cryptographic key 122 is entrusted to a third party, such as hospital or emergency services, as a form of key escrow. Under normal circumstances, the cryptographic key 122 will not be released unless the requester performs proper authentication 129. However, the cryptographic key 122 could be released under specifically-defined circumstances, such as a bona fide medical emergency, to a third party to facilitate access to patient health information in the IMD 103, ambulatory repeater 123, base repeater 124, server 125, programmer 126, or other such authenticated device.

Following authentication 126, the ambulatory repeater 123 can be used to securely transact data exchange sessions with the IMD 103. Each data exchange session is secure in that the patient health information being exchanged is safely protected from compromise and interception by encryption prior to being transmitted. Thus, the communication channel can be unsecured, as the data itself remains protected. As the ambulatory repeater 123 remains physically proximal to the patient, secure data exchange sessions are performed either as on demand or per a schedule, as further described below with reference to FIGS. 6 and 9. Briefly, activation 130 can occur due to a patient-initiated interrogation, on demand or at scheduled times. A patient-initiated interrogation is triggered by a manual override of the ambulatory repeater 123 by the patient when the patient, for instance, feels ill, or otherwise inclined to take a reading of data values. On demand interrogation occurs due to a remote or local event, such as remote activation request from the server 125. Scheduled interrogation is specified by a healthcare provider and remains in effect until a new schedule is downloaded.

Upon activation 130, protected data storage and retrieval 131 and unprotected data storage and retrieval 136 are performed. During protected data storage and retrieval 131, sensitive information 127 (SI), particularly PHI, is provided to and retrieved from the IMD 103, as further described below. During unprotected data storage and retrieval 136, non-sensitive information (non-SI) 135 is retrieved from and sent to the IMD 103 directly via the ambulatory repeater 123. Protected data storage and retrieval 131 and unprotected data storage and retrieval 136 can occur simultaneously during the same data exchange session. In a further embodiment, the SI 127 provided to the IMD 103 can include programming instructions for the IMD 103.

In one embodiment, the bulk of the patient health information retrieved from the IMD 103 is non-SI 135. SI 127 is generally limited to only patient-identifiable health information, which typically does not change on a regular basis. The non-SI 135 loosely falls into two categories of data. First, physiological data relates directly to the biological and biochemical processes of the body, such as salinity, pulse, blood pressure, glucose level, sweat, and so forth. Second, behavioral data relates to physical activities performed by the patient either during the course of a normal day or in response to a specific request or exercise regimen, such as sitting, standing, lying supine, and so forth. Other types of patient health measures are possible.

During protected data storage and retrieval 131, SI 127, particularly PHI, can be received into the ambulatory repeater 123 from one or more sensors 128 and from a patient or clinician, respectively via the base repeater 124 and server 125 or programmer 126. Part or all of the sensitive information 127 is preferably preencrypted using the cryptographic key 122, including any PHI, which can be stored on the IMD 103 as static data for retrieval by health care providers and for use by the IMD 103, such as described in commonly-assigned U.S. Pat. No. 7,475,245, issued Jan. 6, 2009, the disclosure of which is incorporated by reference. If the sensitive information needs to be retrieved, the ambulatory repeater 123 obtains the cryptographic key 122, if necessary, through authentication 126 and retrieves the encrypted information 128 from the IMD 103 for subsequent decryption using the cryptographic key 122. In one embodiment, the sensitive information 127, including any PHI, is encrypted using a standard encryption protocol, such as the Advanced Encryption Standard protocol (AES). Other authentication and encryption techniques and protocols, as well as other functions relating to the use of the cryptographic key 122 are possible, including the authentication and encryption techniques and protocols described in commonly-assigned U.S. Pat. No. 7,155,290, issued Dec. 26, 2006, the disclosure of which is incorporated by reference.

Ambulatory repeater-to-sensor data exchanges 139 enable the ambulatory repeater 123 to receive patient health information from the sensors 138, including external sensors, such as a weight scale, blood pressure monitor, electrocardiograph, Holter monitor, or similar device. In a further embodiment, one or more of the sensors 138 can be integrated directly into the ambulatory repeater 123, as further described below with reference to FIG. 6.

The non-SI 135 and SI 127 is exchanged with at least one of three external data processing devices, which include the base repeater 124, server 125, and programmer 126. In addition, the ambulatory repeater 123 is communicatively interfaced to at least one external sensor to directly measure patient health information, as further described below beginning with reference to FIG. 5. Ambulatory repeater-to-base repeater data exchanges 132 enable the ambulatory repeater 123 to function as a highly portable extension of the base repeater 124. Unlike the base repeater 124, the ambulatory repeater 123 includes a power supply that enables secure interfacing with the IMD 103 while the patient is mobile and away from the base repeater 124 and can interrogate the IMD 103 at any time regardless of the patient's activity level.

Ambulatory repeater-to-server data exchanges 133 enable the server 125 to directly access the IMD 103 via the ambulatory repeater 123 through remote activation, such as in emergency and non-emergency situations and in those situation, in which the base repeater 125 is otherwise unavailable.

Ambulatory repeater-to-programmer data exchanges 134 supplement the information ordinarily obtained during a clinical follow-up session using the programmer 126. The ambulatory repeater 123 interfaces to and supplements the retrieved telemetered data with stored data values that were obtained by the ambulatory repeater 123 on a substantially continuous basis.

In addition, patient health information can be shared directly 137 between the base repeater 124, server 125, and programmer 126. Other types of external data processing devices are possible, including personal computers and other ambulatory repeaters.

Ambulatory Repeater in Handheld Form Factor

Figure 3:
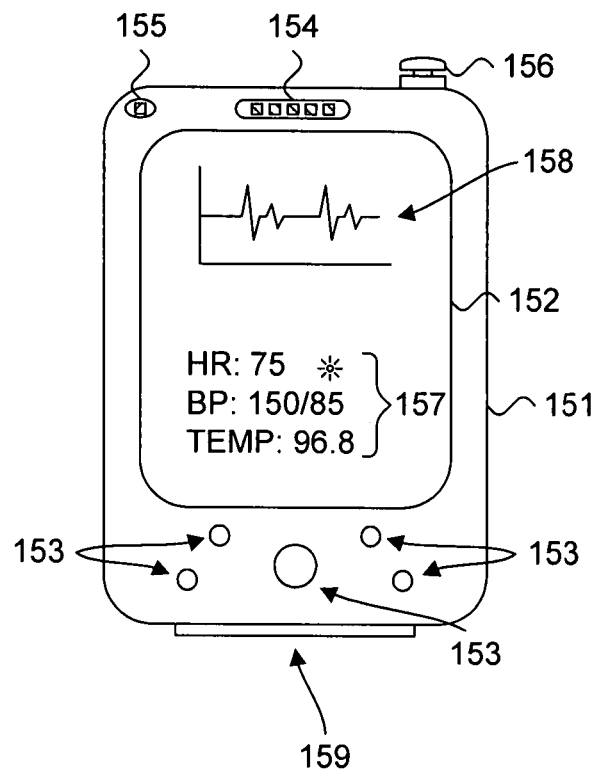
FIG. 3 is a functional block diagram showing, by way of example, an ambulatory repeater in handheld form factor, in accordance with one embodiment.

FIG. 3 is a functional block diagram 150 showing, by way of example, an ambulatory repeater 123 in handheld form factor 151, in accordance with one embodiment. The handheld form factor 151 enables the ambulatory repeater 123 to be carried by the patient and can be implemented as either a stand-alone device or integrated into a microprocessor-equipped device, such as a personal data assistant, cellular telephone or pager. Other types of handheld form factors are possible.

The handheld form factor 151 includes a display 152 for graphically displaying indications and information 157, a plurality of patient-operable controls 153, a speaker 154, and a microphone 155 for providing an interactive user interface. The handheld form factor 151 is preferably interfaced to the IMD 103 through RF telemetry and to the base repeater 124, server 125, and programmer 126 through either RF telemetry, cellular telephone connectivity or other forms of wireless communications, as facilitated by antenna 156. The display 152 and speaker 154 provide visual and audio indicators while the controls 153 and microphone 155 enable patient feedback. In addition, one or more external sensors (not shown) are interfaced or, in a further embodiment, intergraded into the handheld form factor 151 for directly monitoring patient health information whenever required.

The types of indications and information 157 that can be provided to the patient non-exclusively include:

(1) Health measurements
(2) Active or passive pulse generator or health information monitoring (3) Data transmission in-process indication
(4) Alert condition detection
(5) Impending therapy
(6) Ambulatory repeater memory usage
(7) Ambulatory repeater battery charge In addition to securely exchanging data with the IMD 103, the ambulatory repeater 123 can perform a level of analysis of the downloaded telemetered data and, in a further embodiment, provide a further visual indication 158 to the patient for informational purposes.

The handheld form factor 151 can also include a physical interface 159 that allows the device to be physically connected or "docked" to an external data processing device, such as the base repeater 124, for high speed non-wireless data exchange and to recharge the power supply integral to the handheld form factor 151. The ambulatory repeater 123 can continue to securely communicate with the IMD 103, even when "docked", to continue remote communication and collection of telemetered data.

Ambulatory Repeater in Wearable Form Factor

Figure 4:
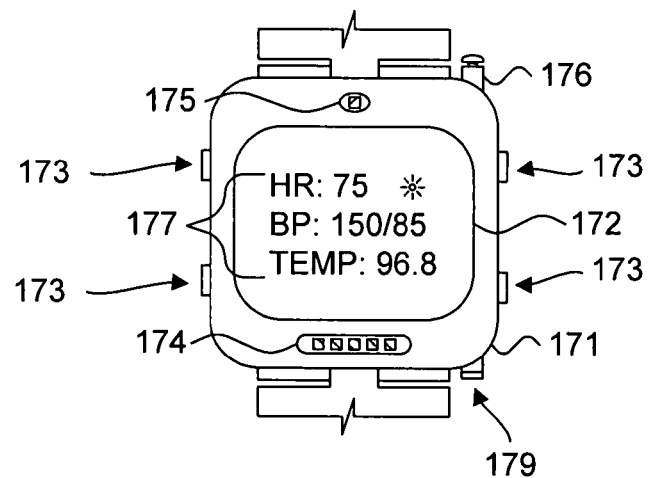
FIG. 4 is a functional block diagram showing, by way of example, an ambulatory repeater in wearable form factor, in accordance with a further embodiment.

FIG. 4 is a functional block diagram 170 showing, by way of example, an ambulatory repeater 123 in wearable form factor 171, in accordance with a further embodiment. The wearable form factor 171 enables the ambulatory repeater 123 to be worn by the patient and can be implemented as either a stand-alone device or integrated into a microprocessor-equipped device, such as a watch or belt. Other types of wearable form factors are possible.

Similar to the handheld form factor 151, the wearable form factor 171 includes a display 172 for graphically displaying indications and information 177, a plurality of patient-operable controls 173, a speaker 174, and a microphone 175 for providing an interactive user interface. The wearable form factor 171 is preferably interfaced to the IMD 103 through RF telemetry and to the base repeater 124, server 125, and programmer 126 through either RF telemetry, cellular telephone connectivity or other forms of wireless communications, as facilitated by antenna 176. The display 172 and speaker 174 provide visual and audio indicators while the controls 173 and microphone 175 enable patient feedback. In addition, one or more external sensors (not shown) are interfaced or, in a further embodiment, intergraded into the wearable form factor 171 for directly monitoring patient health information whenever required. The wearable form factor 171 also includes a physical interface 179 that allows the device to be physically connected or "docked" to an external data processing device.

Ambulatory Repeater System Overview

Figure 5:
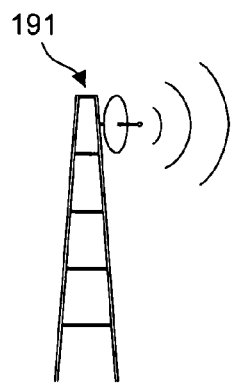
FIG. 5 is a functional block diagram showing, by way of example, systems for securely communicating using an ambulatory repeater, in accordance with one embodiment.
Figure 5:
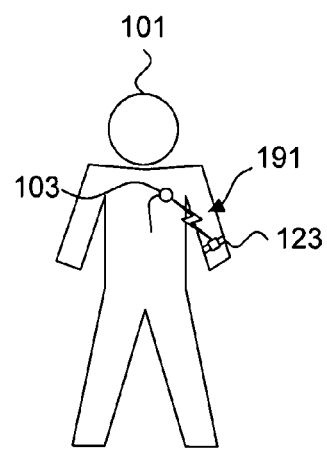
Figure 5:
Figure 5:
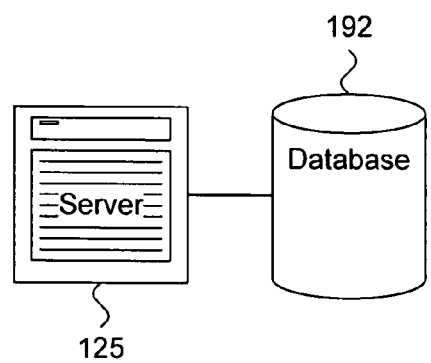
Figure 5:
Figure 5:
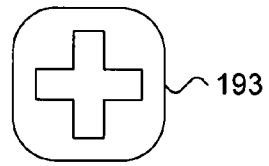

FIG. 5 is a functional block diagram 190 showing, by way of example, systems for securely communicating using an ambulatory repeater 123, in accordance with one embodiment. By way of example, an ambulatory repeater 123 in a wearable form factor 171 is shown, although the ambulatory repeater 123 could also be provided in the handheld form factor 151. The ambulatory repeater 123 securely interfaces to the IMD 103 over a secure data communication interface 191, such as described above with reference to FIG. 2. The ambulatory repeater interrogates the IMD 103 due to a patient-initiated interrogation, on demand, or at scheduled times. Patient-initiated interrogations are triggered by the patient through a manual override of the ambulatory repeater 123. In one embodiment, the patient is limited in the number of times that a patient-initiated interrogation can be performed during a given time period. However, in a further embodiment, a healthcare provider can override the limit on patient-initiated interrogations as required. On demand interrogations occur in response to a remote or local event, such as a health-based event sensed by the ambulatory repeater 123. Scheduled interrogations occur on a substantially regular basis, such as hourly or at any other healthcare provider-defined interval. The schedule is uploaded to the ambulatory repeater 123 and remains in effect until specifically replaced by a new schedule. The ambulatory repeater 123 can also be activated by indirect patient action, such as removing the device from a "docking" station.

Once activated, parametric and behavioral data collected and recorded by the IMD 103 from the external sensors are monitored by the ambulatory repeater 123 in a fashion similar to the base repeater 124. However, the power supply enables the ambulatory repeater 123 to operate separately and independently from external power sources, thereby allowing the patient to remain mobile. The ambulatory repeater 123 also provides the collateral benefits of functioning as an automatic data back-up repository for the base repeater 124 and alleviates patient fears of a lack of monitoring when away from the base repeater 124. In a further embodiment, the parametric and behavioral data is gathered and analyzed by either the ambulatory repeater 123 or an external data processing device, such as repeater 124, server 125 or programmer 126, and provided for review by a healthcare provider. Alternatively, the analysis can be performed through automated means. A set of new IMD parameters can be generated and provided to the ambulatory repeater 123 for subsequent reprogramming of the IMD 103.

Periodically or as required, the ambulatory repeater 123 interfaces to one or more of the base repeater 124, server 125, and programmer 126 to exchange data retrieved from the IMD 103. In one embodiment, the ambulatory repeater 123 interfaces via a cellular network 191 or other form of wireless communications. The base repeater 124 is a dedicated monitoring device specifically matched to the IMD 103. The base repeater 124 relies on external power source and can interface to the IMD 103 either through inductive or RF telemetry. The base repeater 124 further interfaces to the ambulatory repeater 123 either through a physical or wireless connection, as further described above.

The server 125 maintains a database 192 for storing patient records. The patient records can include physiological quantitative and quality of life qualitative measures for an individual patient collected and processed in conjunction with, by way of example, an implantable medical device, such a pacemaker, implantable cardiac defibrillator (ICD) or similar device; a sensor 138, such as a weight scale, blood pressure monitor, electrocardiograph, Holter monitor or similar device; or through conventional medical testing and evaluation. In addition, the stored physiological and quality of life measures can be evaluated and matched by the server 123 against one or more medical conditions, such as described in related, commonly-owned U.S. Pat. No. 6,336,903, to Bardy, issued Jan. 8, 2002; U.S. Pat. No. 6,368,284, to Bardy, issued Apr. 9, 2002; U.S. Pat. No. 6,398,728, to Bardy, issued Jun. 2, 2002; U.S. Pat. No. 6,411,840, to Bardy, issued Jun. 25, 2002; and U.S. Pat. No. 6,440,066, to Bardy, issued Aug. 27, 2002, the disclosures of which are incorporated by reference.

The programmer 126 provides conventional clinical follow-up of the IMD 103 under the direction of trained healthcare professionals. In one embodiment, the ambulatory repeater 123 interfaces via a cellular network 191 or other form of wireless communications. Other types of external data processing devices and interfacing means are possible.

In a further embodiment, the ambulatory repeater 123 interfaces to emergency services 193, which posses a copy of the cryptographic key 122 (shown in FIG. 2) held in a key escrow. Under ordinary circumstances, patient health information is exchanged exclusively between the ambulatory repeater 123 and authenticated external data processing devices, such as the base repeater 124, server 125, and programmer 126. However, in a bona fide emergency situation, the emergency services 193 can use the cryptographic key 122 to access the patient health information in the ambulatory repeater 123 and IMD 103, as well as the repeater 124, server 125, and programmer 126. Other forms of key escrow are possible.

Ambulatory Repeater Internal Components

Figure 6:
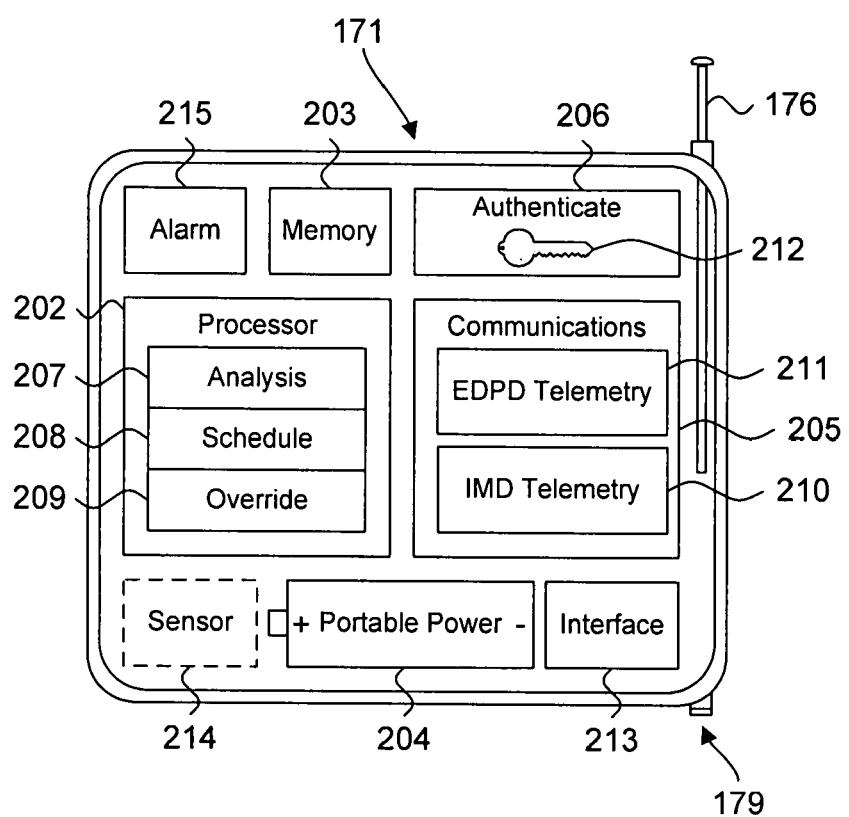
FIG. 6 is a functional block diagram showing, by way of example, the internal components of the ambulatory repeater in the wearable form factor of FIG. 4.

FIG. 6 is a functional block diagram 190 showing, by way of example, the internal components of the ambulatory repeater 123 in the wearable form factor 171 of FIG. 4. By way of example, the ambulatory repeater 123 includes a processor 202, memory 203, authentication module 212, communications module 205, physical interface 213, optional integrated sensor 214, and alarm 215. Each of the components is powered by a power supply 204, such as a rechargeable or replaceable battery. The internal components are provided in a housing 201 with provision for the antenna 176 and physical interface 179.

The processor 202 enables the ambulatory repeater 123 to control the authentication and secure transfer of both non-sensitive and sensitive information between the IMD 103, one or more external sensors (not shown), and one or more of the base repeater 124, server 125, and programmer 126. The processor 202 also operates the ambulatory repeater 123 based on functionality embodied in an analysis module 207, schedule module 208 and override module 209. The analysis module 207 controls the translation, interpretation and display of patient health information. The schedule module 208 controls the periodic interfacing of the ambulatory repeater 123 to the IMD 103 and external data processing device. The override module 209 controls the patient-initiated interrogation. Other control modules are possible.

The communications module 205 includes an IMD telemetry module 210 and external data processing device (EDPD) telemetry module 211 for respectively interfacing to the IMD 103 and external data processing device, such as the base repeater 124, server 125, and programmer 126. Preferably, the ambulatory repeater 123 interfaces to the IMD 103 and external sensors through inductive RF telemetry, Bluetooth, or other form of secure wireless interface, while the ambulatory repeater 123 interfaces to external data processing device preferably through RF telemetry or via cellular network or other form of wireless interface. The authentication module 206 is used to securely authenticate and encrypt and decrypt sensitive information using a retrieved cryptographic key 212. The memory 203 includes a memory store, in which the physiological and parametric data retrieved from the IMD 103 are transiently stored pending for transfer to the external data processing device and, in a further embodiment, download to the IMD 103. The physical interface 213 controls the direct physical connecting of the ambulatory repeater 123 to an external data processing device or supplemental accessory, such as a recharging "dock" or other similar device. The optional integrated sensor 214 directly monitors patient health information, such as patient activity level. Lastly, the alarm 215 provides a physical feedback alert to the patient, such as through a visual, tactual or audible warning, for example, flashing light, vibration, or alarm tone, respectively. Other internal components are possible, including a physical non-wireless interface and removable memory components.

Ambulatory Repeater Method Overview

Figure 7:
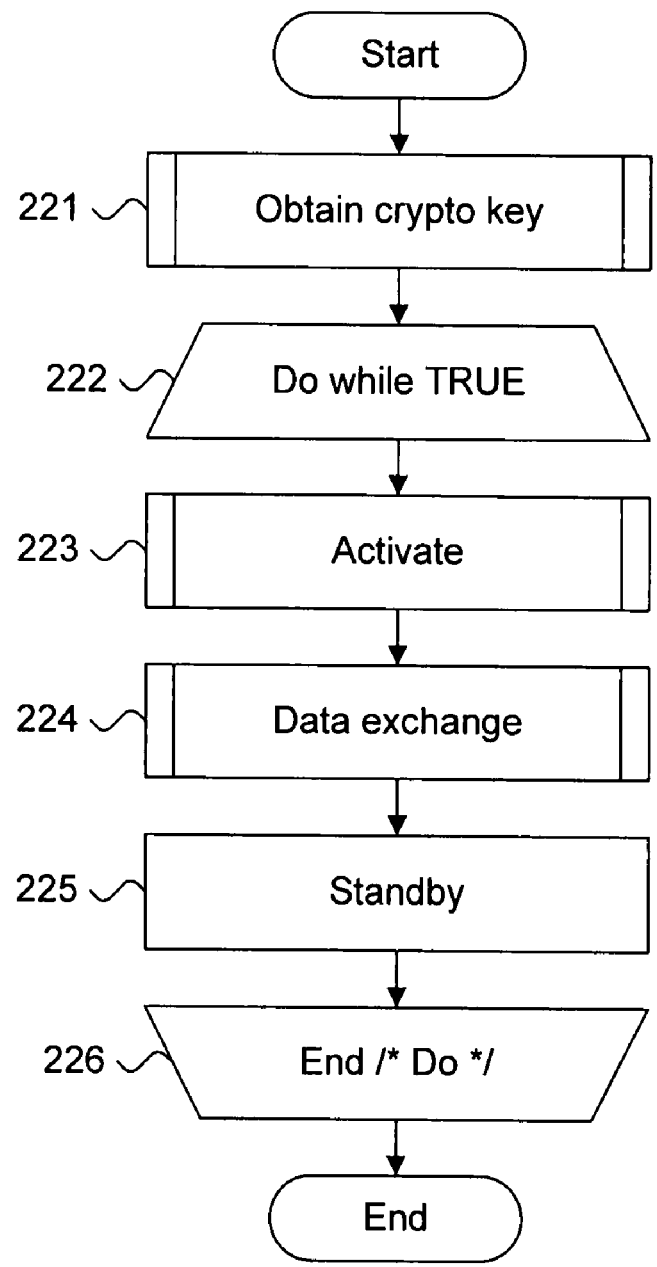
FIG. 7 is a flow diagram showing a method for providing automated patient care using an ambulatory repeater, in accordance with one embodiment.

FIG. 7 is a flow diagram showing a method 220 for providing automated patient care using an ambulatory repeater 123, in accordance with one embodiment. The purpose of this method is to periodically activate and securely exchange information with the IMD 103, one or more sensors 138, and an external data processing device that includes one or more of a base repeater 124, server 125, and programmer 126. The method 220 is described as a sequence of process operations or steps, which can be executed, for instance, by an ambulatory repeater 123.

The method begins by obtaining the cryptographic key 122 (block 221), as further described below with reference to FIG. 8. The method then iteratively processes data exchange sessions (blocks 222-226) as follows. First, the ambulatory repeater 123 is activated (block 223), which includes securely interrogating the IMD 103, as further described below with reference to FIG. 9. Next, the ambulatory repeater 123 performs a data exchange session with one or more of the external data processing devices, including the base repeater 124, server 125, and programmer 126, as further described below with reference to FIG. 10. Following completion of the data exchange session, the ambulatory repeater 123 returns to a stand-by mode (block 225). Processing continues (block 226) while the ambulatory repeater 123 remains in a powered-on state.

Obtaining a Cryptographic Key

Figure 8:
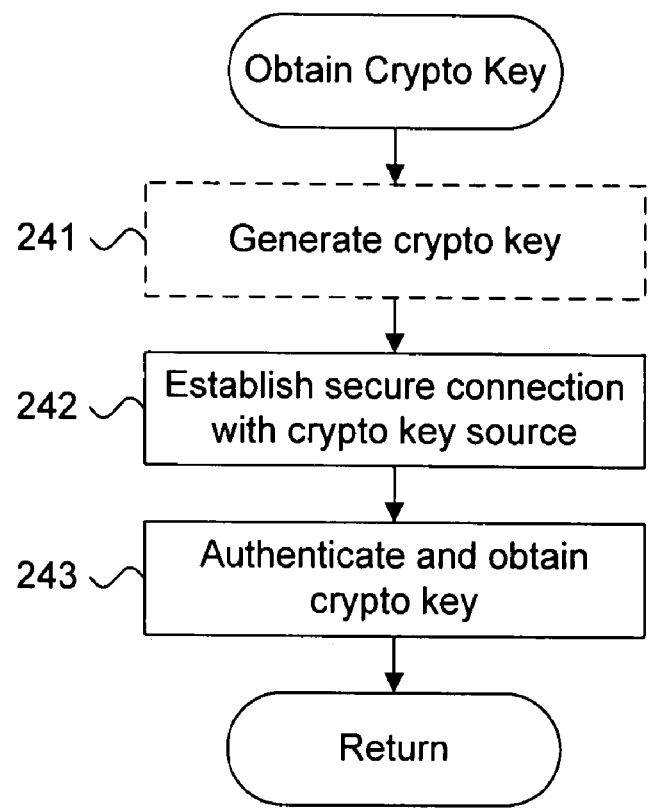
FIG. 8 is a flow diagram showing a routine for obtaining a cryptographic key for use in the method of FIG. 7.

FIG. 8 is a flow diagram showing a routine 240 for obtaining a cryptographic key 122 for use in the method 220 of FIG. 7. The purpose of this routine is to securely receive the cryptographic key uniquely assigned to the IMD 103 into the ambulatory repeater 123.

Initially, the cryptographic key 122 is optionally generated (block 241). Depending upon the system, the cryptographic key 122 could be generated dynamically by the base repeater 124 or programmer 126 for subsequent download to the IMD 103 using short range telemetry following implantation. Similarly, the cryptographic key 122 could be generated during the manufacturing process and persistently stored in the IMD 103 prior to implantation. Alternatively, the cryptographic key 122 could be dynamically generated by the IMD 103.

Next, a secure connection is established with the source of the cryptographic key 122 (block 242). The form of the secure connection is dependent upon the type of key source. For instance, if the key source is the IMD 103, the secure connection could be established through inductive or secure RF telemetric link via the base repeater 124 or programmer 126. If the key source is the base repeater 124, a secure connection could be established through the dedicated hardwired connection.

Finally, the cryptographic key 122 is authenticated and obtained (block 243) by storing the cryptographic key 122 into the authentication module 206.

Ambulatory Repeater Activation

Figure 9:
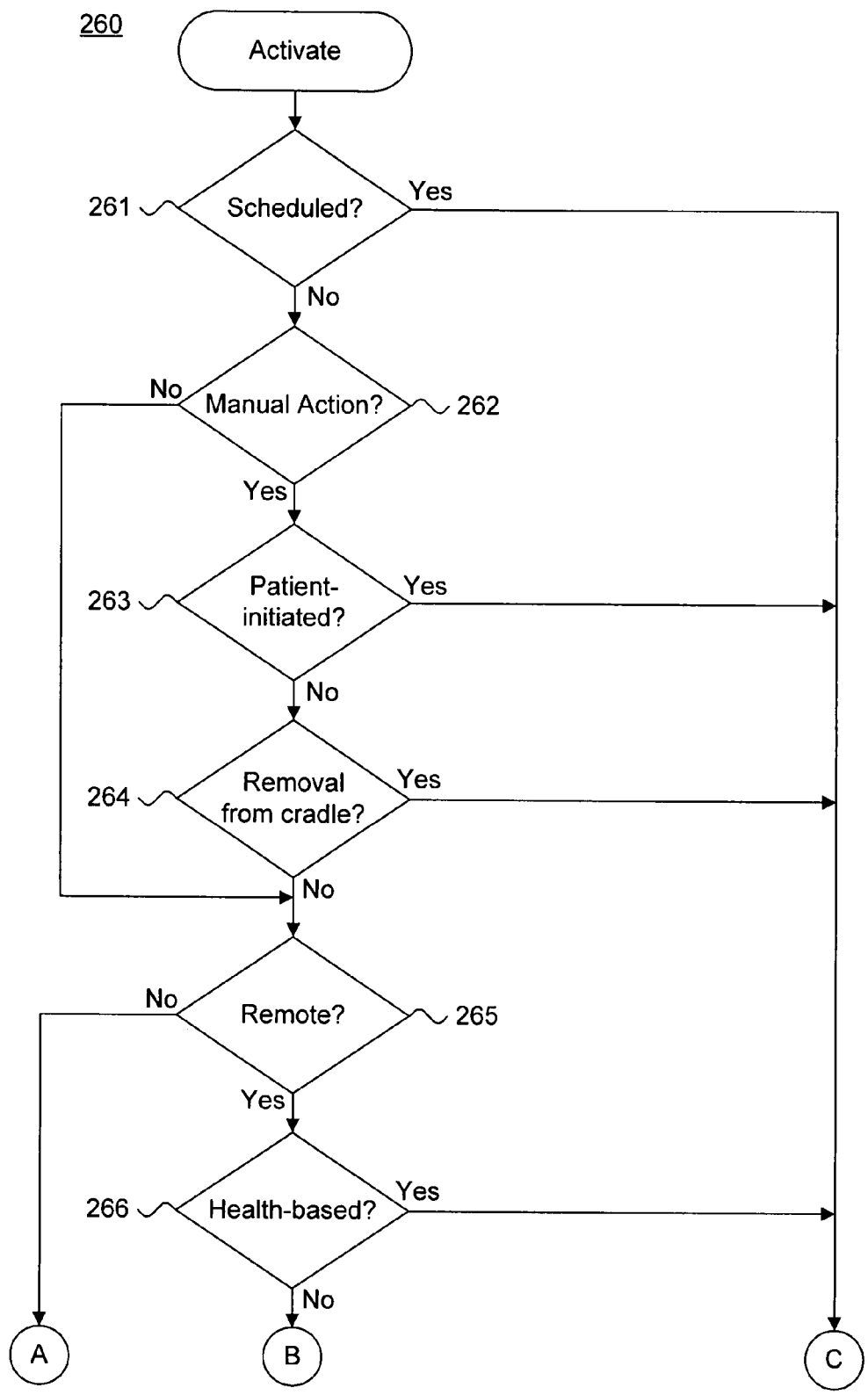
FIG. 9 is a flow diagram showing a routine for activating an ambulatory repeater for use in the method of FIG. 7.
Figure 9:
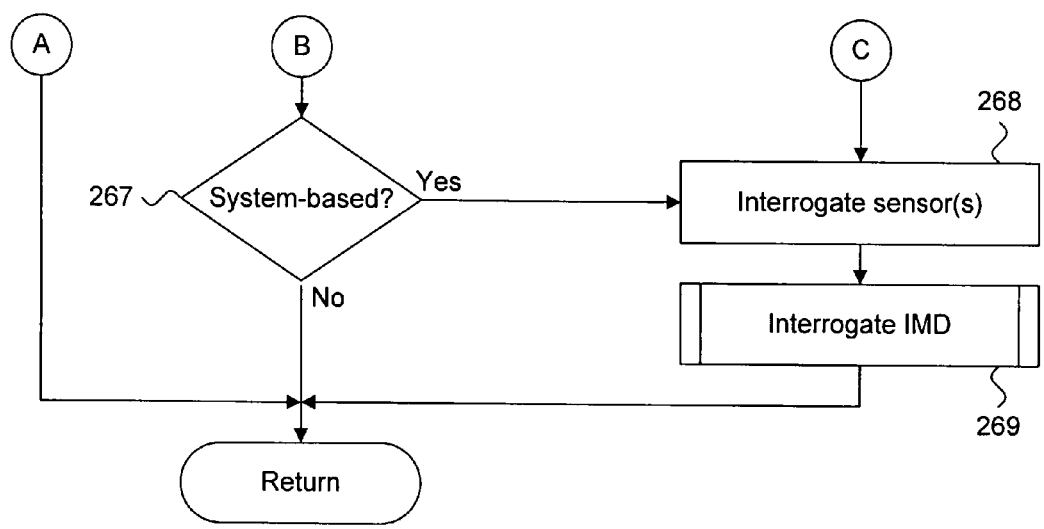

FIG. 9 is a flow diagram showing a routine 260 for activating an ambulatory repeater 123 for use in the method 220 of FIG. 7. The purpose of the routine is to activate the ambulatory repeater 123 prior to interrogating the sensors 138 and IMD 103.

The ambulatory repeater 123 can be activated as scheduled (block 261) or through manual action directly or indirectly by the patient (block 262) or remotely, such as by the server 125 (block 265).

Manual activation typically involves either a direct patient-initiated interrogation (block 263), such as operating a manual override control, or indirect action, such as removing the ambulatory repeater 123 from a "docking" cradle (block 264). Similarly, remote activation involves either health-based data transfer triggers (block 266) or system-based data transfer triggers (block 267). A health-based data transfer is triggered when a prescribed or defined health status or alert condition is detected. A system-based data transfer trigger occurs typically due to a device-specific circumstance, such as data storage nearing maximum capacity. Other forms of manual and remote ambulatory repeater activations are possible. Upon activation, the sensors 138 and IMD 103 are interrogated (blocks 268 and 269), as further described below with reference to FIG. 11.

Secure Data Exchange

Figure 10:
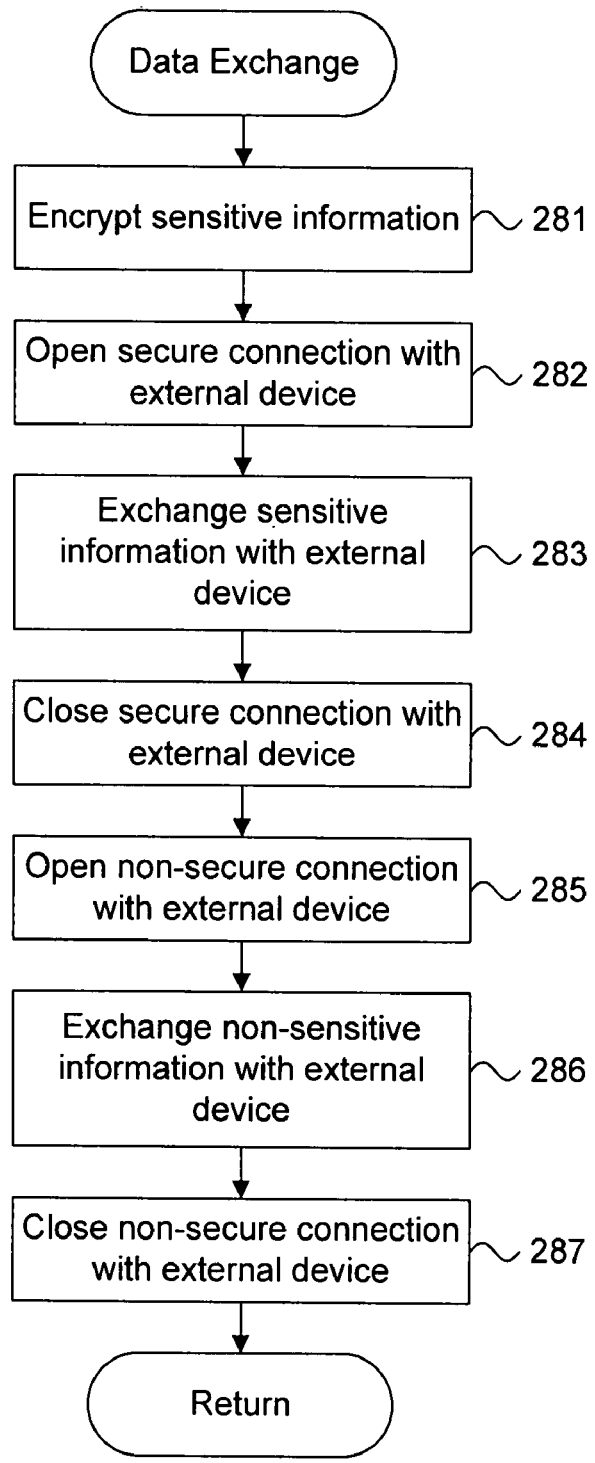
FIG. 10 is a flow diagram showing a routine for performing a secure data exchange for use in the method of FIG. 7.

FIG. 10 is a flow diagram showing a routine 280 for performing a secure data exchange for use in the method 220 of FIG. 7. The purpose of this routine is to exchange data between the ambulatory repeater 123 and one or more external data processing device, such as the base repeater 124, server 125, and programmer 126.

Initially, any sensitive information 127 is encrypted (block 281) using, for instance, the cryptographic key 122 that is uniquely assigned to the IMD 103, or other cryptographic key (not shown) upon which the ambulatory repeater 123 and external data processing device have previously agreed. A secure connection is opened with the external data processing device (block 282) and the sensitive information is exchanged (block 283). The connection is "secure" in that the sensitive information is only exchanged in an encrypted or similar form protecting the sensitive information from compromise and interception by unauthorized parties. In the described embodiment, the secure connection is served through a Web-based data communications infrastructure, such as WebSphere software, licensed by IBM Corporation, Armonk, N.Y. Other types of data communications infrastructures can be used. Upon the competition of the exchange of sensitive information, the secure connection with external data processing device is closed (block 284) and a non-secure connection is open (block 285). Similarly, non-sensitive information is exchanged (block 286) and the non-secure connection is closed (block 287). The non-sensitive information can be sent in parallel to the sensitive information and can also be sent over the secure connection. However, the sensitive information cannot be sent over the non-secure connection.

IMD Interrogation

Figure 11:
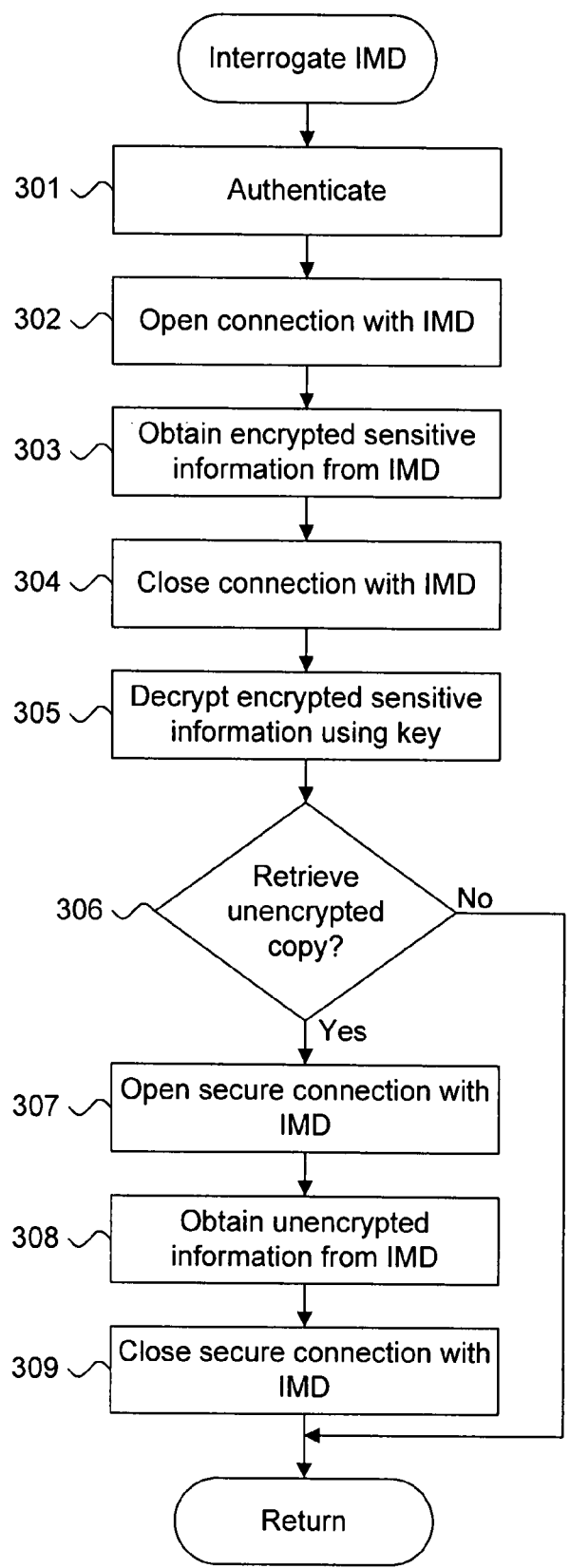
FIG. 11 is a flow diagram showing a routine for interrogating an IMD for use in the method of FIG. 7.

FIG. 11 is a flow diagram showing a routine 300 for interrogating an IMD 103 for use in the method 220 of FIG. 7. The purpose of this routine is to retrieve encrypted sensitive information 128, including any PHI, from the IMD 103 and to decrypt the encrypted sensitive information 128 using the cryptographic key 122 uniquely assigned to the IMD 103.

Initially, the ambulatory repeater 123 authenticates with the IMD 103 (block 301). A connection is established between the IMD 103 and the ambulatory repeater 123 (block 302) via an RF connection. Encrypted sensitive information 127, including any PHI, is retrieved from the IMD 103 (block 303) and the connection between the IMD 103 and the ambulatory repeater 123 is closed (block 304). The encrypted sensitive information 128 is then decrypted using the cryptographic key 122 (block 305).

While the invention has been particularly shown and described as referenced to the embodiments thereof, those skilled in the art will understand that the foregoing and other changes in form and detail may be made therein without departing from the spirit and scope of the invention.

What is claimed is:

1. A secure wireless ambulatory repeater system, comprising:
    an implantable medical device comprising a secure key repository for maintaining one or more cryptographic keys; and
    a secure wireless ambulatory repeater comprising:
        a memory for storing sensitive information preencrypted under a cryptographic key and physiological measures measured by the implantable medical device;
        an authentication module to securely obtain the cryptographic key from the secure key repository of the implantable medical device;
        a processor comprising:
            a decryption module to decrypt the sensitive information with the cryptographic key into decrypted information; and
            a communications module to exchange the decrypted information and the physiological measures with an external data processing device over a wireless interface contingent upon authorization of the external data processing device;
        wherein the ambulatory repeater is consists of one of a wearable or handheld form factor.

2. An ambulatory repeater according to claim 1, further comprising:
    a telemetry interface to the implantable medical device over which the cryptographic key, the sensitive information, and the physiological measures are securely received.

3. An ambulatory repeater according to claim 2, wherein the telemetry interface operates over at least one of inductive telemetry, radio frequency telemetry, and Bluetooth telemetry.

4. An ambulatory repeater according to claim 1, wherein the cryptographic key is maintained in a key escrow.

5. An ambulatory repeater according to claim 1, wherein the physiological measures are measured by a sensor comprised in the implantable medical device.

6. An ambulatory repeater according to claim 1, further comprising:
    an activation module to transition the ambulatory repeater from a standby mode; and
    a standby module to transition the ambulatory repeater from an active mode.

7. An ambulatory repeater according to claim 6, wherein the activation module is at least one of internally triggered by at least one of a schedule, an alert condition, and a manual override, and remotely triggered by the external data processing device.

8. An ambulatory repeater according to claim 1, wherein the physiological measures comprises one or more of physiological and behavioral data.

9. An ambulatory repeater according to claim 1, wherein the external data processing device is selected from the group comprising a server, personal computer, repeater, and programmer.

10. An ambulatory repeater system for use in automated patient care, comprising:
    an implantable medical device comprising a secure key repository for maintaining one or more cryptographic keys; and
    an ambulatory repeater comprising:
        a local memory store, comprising:
            a cryptographic key uniquely assigned to an implantable medical device; and
            sensitive information preencrypted under the cryptographic key and physiological measures measured by the implantable medical device;
        a processor operatively coupled to the local memory store, comprising:

an authentication module to receive the cryptographic key from the implantable medical device, further comprising:
    a permissions module to confirm authorization of an external data processing device against the cryptographic key; and
    a decryption module to decrypt the sensitive information with the cryptographic key into decrypted information; and
    a communications module to exchange the decrypted information and the physiological measures with the external data processing device over a wireless interface contingent upon the authorization confirmation; and
an internal power supply to supply power to the foregoing components;
wherein the ambulatory repeater is selected from the group consisting of a wearable form factor and a handheld form factor.

11. An ambulatory repeater system according to claim 10, wherein the processor further comprises one or more of:
    an analysis module, which includes functionality comprising one or more of analysis, translation, interpretation, and display of the decrypted information and the physiological measures;
    a schedule module to control periodic exchange of the sensitive information and the physiological measures with the implantable medical device and the external data processing device; and
    an override module to control on-demand interrogation of the implantable medical device.

12. An ambulatory repeater system according to claim 10, wherein the wireless interface is selected from the group comprising radio frequency telemetry and cellular telemetry.

13. An ambulatory repeater system according to claim 10, wherein the physiological measures are selected from the group comprising pulse, blood pressure, glucose level, sweat, patient ambulatory activities, weight, salinity, cumulative totals of sensed and paced events, transmission of electrograms, pacing, cardiac health information monitoring, alert condition detection, impending therapy resynchronization, defibrillation, neural stimulation, and drug delivery measures.

14. An ambulatory repeater system according to claim 10, the ambulatory repeater further comprising:
    a user operable interface, comprising:
        user-operable input controls, which are selected from the group comprising a keyboard, a pointing device, a microphone, and a button array; and
        user-perceptible output devices, which are selected from the group comprising a display, a speaker, and a tactile feedback generator.

15. An ambulatory repeater system according to claim 10, the ambulatory repeater further comprising:
    an alarm generator comprising a trigger, which is tripped whenever one or more of a health-based condition and a device-specific circumstance occurs.

16. An ambulatory repeater system according to claim 10, wherein the internal power supply is selected from the group comprising a rechargeable battery and a replaceable battery.

* * * * *

UNITED STATES PATENT AND TRADEMARK OFFICE
CERTIFICATE OF CORRECTION

| | | |
|---|---|---|
| PATENT NO. | : 7,967,751 B2 | Page 1 of 1 |
| APPLICATION NO. | : 11/893704 | |
| DATED | : June 28, 2011 | |
| INVENTOR(S) | : Donald L. Goscha et al. | |

It is certified that error appears in the above-identified patent and that said Letters Patent is hereby corrected as shown below:

Col. 14, line 19, claim 1: "repeater is consists of" should read "repeater consists of"

Signed and Sealed this
Eighth Day of November, 2011

David J. Kappos
*Director of the United States Patent and Trademark Office*